United States Patent [19]
Maes

[11] Patent Number: 4,628,204
[45] Date of Patent: Dec. 9, 1986

[54] OPTICAL METHOD TO STUDY THE STABILITY OF COLLOIDAL SYSTEMS

[75] Inventor: Jean Pierre Maes, Merebeke, Belgium

[73] Assignee: S.A. Texaco Belgium N.V., Brussels, Belgium

[21] Appl. No.: 641,228

[22] Filed: Aug. 16, 1984

[51] Int. Cl.$^4$ .............................................. G01N 21/27
[52] U.S. Cl. .................................... 250/343; 210/745; 356/442
[58] Field of Search ............... 250/343, 373, 301, 574, 250/575, 573, 432 R, 345; 356/70, 436, 442, 338; 73/61.4; 210/726, 745

[56] References Cited

U.S. PATENT DOCUMENTS

| | | | |
|---|---|---|---|
| 3,263,553 | 8/1966 | Baruch | 250/573 |
| 3,572,930 | 3/1971 | Morcom et al. | 250/575 |
| 3,814,930 | 6/1974 | Lindberg | 356/442 |
| 4,113,386 | 9/1978 | Lepper, Jr. | 356/442 |
| 4,170,533 | 10/1979 | Lang et al. | 210/745 |
| 4,207,450 | 6/1980 | Mittleman | 250/343 |
| 4,348,112 | 9/1982 | Moreaud et al. | 356/338 |

FOREIGN PATENT DOCUMENTS

| | | | |
|---|---|---|---|
| 3143825 | 5/1983 | Fed. Rep. of Germany | 210/745 |
| 2432482 | 4/1980 | France | 210/745 |

Primary Examiner—Carolyn E. Fields
Attorney, Agent, or Firm—Robert A. Kulason; James J. O'Loughlin; Robert B. Burns

[57] ABSTRACT

Method and apparatus for continuous measurement and control of the stability of colloidal systems such as heavy fuel oils, using an optical procedure with near-infrared radiation. A stream of liquid representing the colloidal system is passed through a loop or elongated conduit. In the latter, measured amounts of a flocculating agent is progressively added to the stream at a series of spaced apart stations in the loop which define separate segments. These additions progressively enhance the amount of flocculating agent to the colloidal liquid to a point where flocculation occurs. The character of each segment of the loop is tested by irradiation whereby the mixture in each segment is measured to determine in which segment flocculation has commenced. A suitable signal, whether audible or visual, can then be provided to indicate the occurrence.

14 Claims, 10 Drawing Figures

FIG. 2a
FIG. 2b
FIG. 2c
FIG. 3
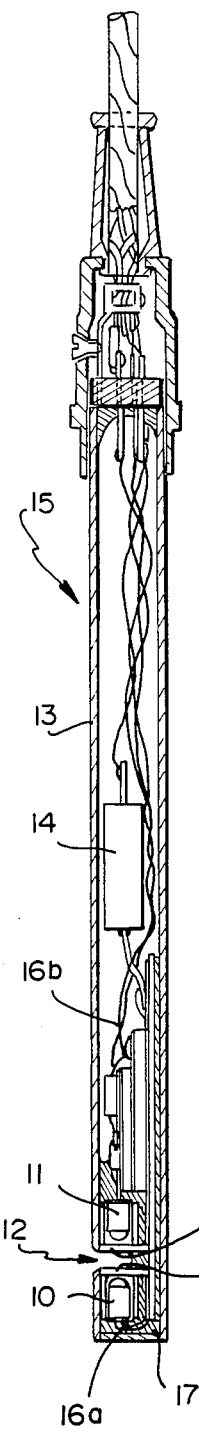
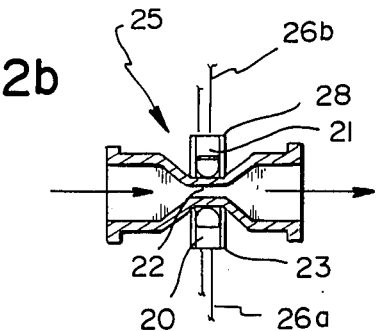
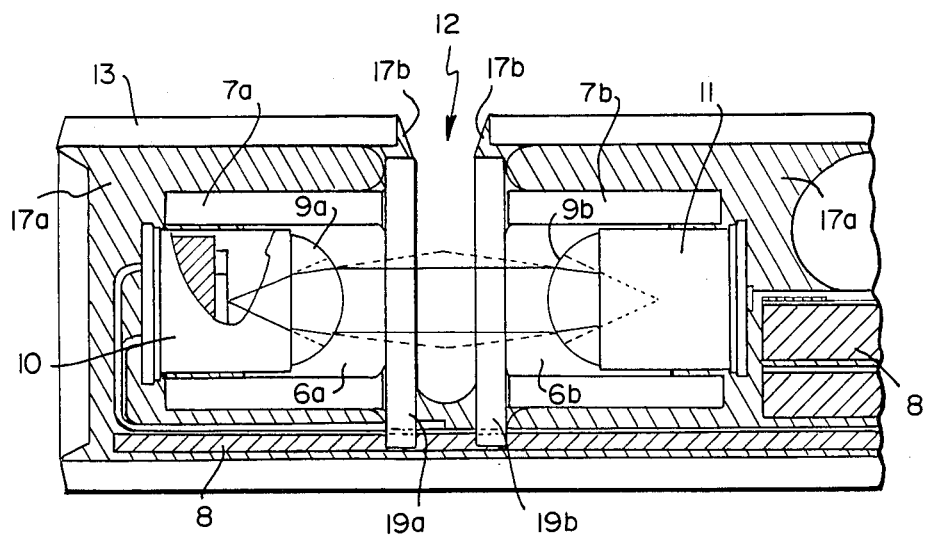
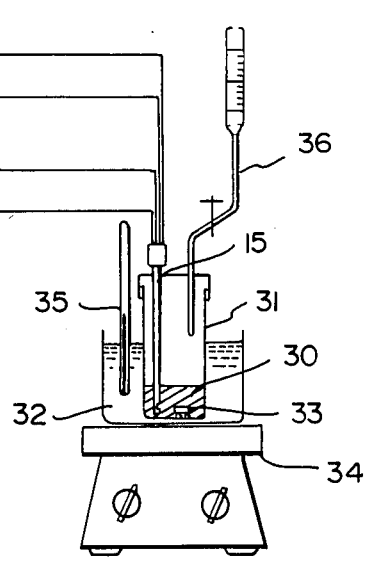

OPTICAL METHOD TO STUDY THE STABILITY OF COLLOIDAL SYSTEMS

BACKGROUND OF THE INVENTION

Heavy fuel oils can be considered as colloidal systems, in which asphaltenes with high C/H ratio are peptized as micelles in an oily phase. An important characteristic of colloidal systems, which distinguishes them from true solutions, is the presence of particles which are larger than molecules. The stability of a colloidal system typically depends on its ability to maintain the particles in solution and thus to prevent aggregation and precipitation. This stability in a fuel oil depends on the state of peptization, P, of the asphaltenes present, and the state of peptization depends in turn on both the peptizing (or solvent) power, $P_o$, of the fuel oil medium and the peptizability (or solubility), $P_a$, of the asphaltenes.

A publication, van Kerkvoort et al, Paper No. 229, IV Congres International du Chauffage Industriel, Paris, 1952, hereafter called the Reference, describes a method for evaluating the stability of fuel oils and the compatibility of fuel oil blends by mans of a Flocculation Ratio test. A procedure is given by the Reference for determining the minimum percentage aromatics that a test mixture of aromatic and paraffinic hydrocarbons should have which, when added to the fuel oil at a given dilution ratio, just fails to cause flocculation of the asphaltenes present in the fuel oil. This minimum percentage aromatics is called the Flocculation Ratio.

This Flocculation Ratio is determined in the Reference by making time consuming and laborious batch measurements involving a Spot Test, while this invention provides accurate method and apparatus for making the same measurements rapidly and continuously. The Flocculation Ratio (FR) is determined according to the Reference at different dilution ratios (DR) of the aromatic-non aromatic hydrocarbon mixture (e.g. toluene and n-heptane) and the fuel oil, after which a curve is obtained expressing the relation between the degree of dilution of the fuel oil and the minimum aromatic content (FR) that the aromatic-non aromatic hydro-carbon mixture should have in order to avoid asphaltene flocculation, that is, so that the asphaltenes are just peptized. The curve expressing this relation is preferably plotted as Flocculation Ratio versus the inverse of the dilution ratio, or FR versus 1/DR. It has been verified experimentally that such a plot is linear for a wide range of residual fuels and fuel oil blends. The linear plot versus 1/DR is preferred over the non-linear plot versus DR, since extrapolations can be made with better accuracy with the linear plot. An example of such a plot is shown in FIG. 1a, where DR is expressed as volume of diluent divided by mass of fuel. DR is sometimes expressed as volume of diluent divided by volume of fuel, but the conversion between these two forms of DR will present no problem.

An important and useful property of the FR versus 1/DR plot is that the intercept on the ordinate axis ($FR_{max}$) and the intercept on the abscissa axis ($DR_{min}$) provide the state of peptization, P, the peptizing power, $P_o$, and the peptizability, $P_a$, by the following formulas:

$$P_o = FR_{max}(DR_{min}+1)$$

$$P_a = 1 - FR_{max}$$

$$P = P_o/(1-P_a) = DR_{min}+1;$$

and furthermore, what is of particular practical significance when blending is involved, $P_o$ and $P_a$ are additive. Thus the stability/compatibility of a fuel oil blend can be calculated from the $P_o$ and $P_a$ values of the components used. For example, for a binary blend, the following equations are valid:

$$P_{oblend} = V_1 P_{o1} + V_2 P_{o2} \tag{1}$$

$$P_{ablend} = (V_1 M_1 P_{a1} + V_2 M_2 P_{a2})/(V_1 M_1 + V_2 M_2) \tag{2}$$

$$P_{blend} = P_{o\ blend}/(1 - P_{a\ blend}) \tag{3}$$

where V is the volume fraction of each blending component and M its asphaltene content.

The physical significance of the quantities in the above equations is summarized:

FR: Flocculation Ratio: is the minimum aromatic content that an aromatic-non aromatic hydrocarbon mixture should have in order to dilute a fuel oil to DR volumes without causing flocculation of the asphaltenes.

DR: The number of volumes of dilution liquid per volume of fuel oil phase (asphaltene dispersion).

$FR = f(DR)$: The curve represents the flocculation ratio (FR) as a function of the degree of dilution (with aromatic/non aromatic mixtures at different ratios); the curve gives the limiting conditions for a fuel oil at which the asphaltenes of an asphaltene dispersion are still peptized.

$DR_{min}$: Is the maximum volume of non-aromatic hydrocarbon (FR=0) with which the fuel oil can be diluted without asphaltenes flocculation.

At infinite dilution of the asphaltene dispersion with an aromatic-non aromatic hydrocarbon mixture:

$FR_{max}$: Is the aromatic content of the diluent liquid required to keep the asphaltenes peptized (at infinite dilution the peptizing power of the fuel oil medium is determined only by the diluent liquid).

$1-FR_{max}$: Is the non-aromatic content at infinite dilution which can be tolerated without causing asphaltene flocculation.

$P_a$: Is defined as the peptizability of the asphaltenes and is equal to $1-FR_{max}$. The better the peptizability of the asphaltenes, the higher $1-FR_{max}$ will be.

$P_o$: Is the peptizing power of the fuel oil medium and can be defined as the aromatic equivalent of this fuel oil expressed in volume percent of the aromatic component of an aromatic-non aromatic hydrocarbon mixture having the same peptizing power as the fuel oil.

P: Is the state of peptization of the asphaltenes in a fuel oil and is equal to $P_o/(1-P_a)$, indicating that the state of peptization becomes better the higher the peptizing power of the fuel oil medium and the better the asphaltenes can be peptized. If P > 1 the fuel oil (blend) will remain free of dry sludge (stable fuel with asphaltenes peptized), otherwise (P < 1) the asphaltenes will flocculate (unstable fuel oil).

BRIEF SUMMARY OF THE INVENTION

In assessing the stability and stability limits of heavy fuel oils and their compatibility with other fuel oils and with cutter stocks it is necessary to know under what conditions flocculation or the formation of floccular aggregates, such as the precipitation of asphaltenes, occurs. A conventional method for determining the occurrence of flocculation is the ASTM Spot Test, Designation D 2781, "Standard Method of Test for Compatibility of Fuel Oil Blends by Spot Test" or a modification of that Test. These conventional methods are time consuming and laborious, as they involve the preparation of numerous solutions, all to be checked for the occurrence of flocculation. This invention provides an optical titration method which is rapid and accurate and also is adaptable for use in a continuous on-line process analyzer.

THE DRAWINGS

The foregoing and other objects and benefits of the invention will be more fully set forth below in connection with the best mode contemplated by the inventor of carrying out the invention, and in connection with which there are illustrations provided in the drawings, wherein:

FIGS. 1a, 1b, 1c, and 1d illustrate how measurements made with the apparatus of the invention are plotted graphically to determine stability properties of colloidal systems.

FIGS. 2a and 2b illustrate the optical probe or cell for use in laboratory or batch measurement and continuous measurement respectively.

FIG. 2c illustrates a detail of the optical probe of FIG. 2a.

FIG. 3 illustrates apparatus of the invention for making laboratory or batch measurements.

DESCRIPTION OF THE PREFERRED EMBODIMENT

Interaction of Radiation with Matter

When radiation from a light source passes through a sample of optically dense material, the radiation which is transmitted equals the difference between the incident radiation and the radiation absorbed or scattered by the sample. Absorbed radiation may be converted into heat or radiated as fluorescence. Incident radiation is scattered by the molecules of the sample (Rayleigh scattering) or by small particles or inhomogeneties in the sample (Tyndall scattering).

The transmission of radiation in a colloidal solution will depend on the absorbing and scattering properties of the medium, which is determined by the absorbing properties and the refractive index of the colloidal particles and of any floccular aggregates formed from those particles, as well as by their size relative to the wavelength of the incident radiation. It has been found that with the selection of a radiation source of suitable wavelength, significant changes in transmitted radiation can be observed when a colloidal solution (such as a heavy fuel oil) becomes unstable, and particle size (e.g. of the asphaltenes) is increased by aggregation.

Laboratory or Batch Measurement

According to this invention an optical probe, to be described in detail hereinbelow, is used in a titration procedure to make rapid and accurate observations of the occurrence of flocculation, i.e. the formation of floccular aggregates, on the basis of light absorption or scattering by the precipitated asphaltenes, and thus to determine the desired values of FR. Although the description which follows is concerned with reduction in intensity of transmitted radiation as an indicator of flocculation, it should be understood that flocculation is also indicated by an increase in intensity of scattered radiation, and both phenomena are within the scope of this invention.

Prior art relevant to the subject matter of this invention may be found in the following publication and the bibliography thereof: "Action de divers diluants sur les produits petroliers lourds: mesure, interpretation et prevision de la floculation des asphaltenes", by G. Hotier and M. Robin, Revue de l'Institut Francais du Petrole, Vol. 38, No. 1, Jan/Feb 1983. This invention is concerned with improved forms of apparatus for observing the occurrence of flocculation.

Figure 1A:
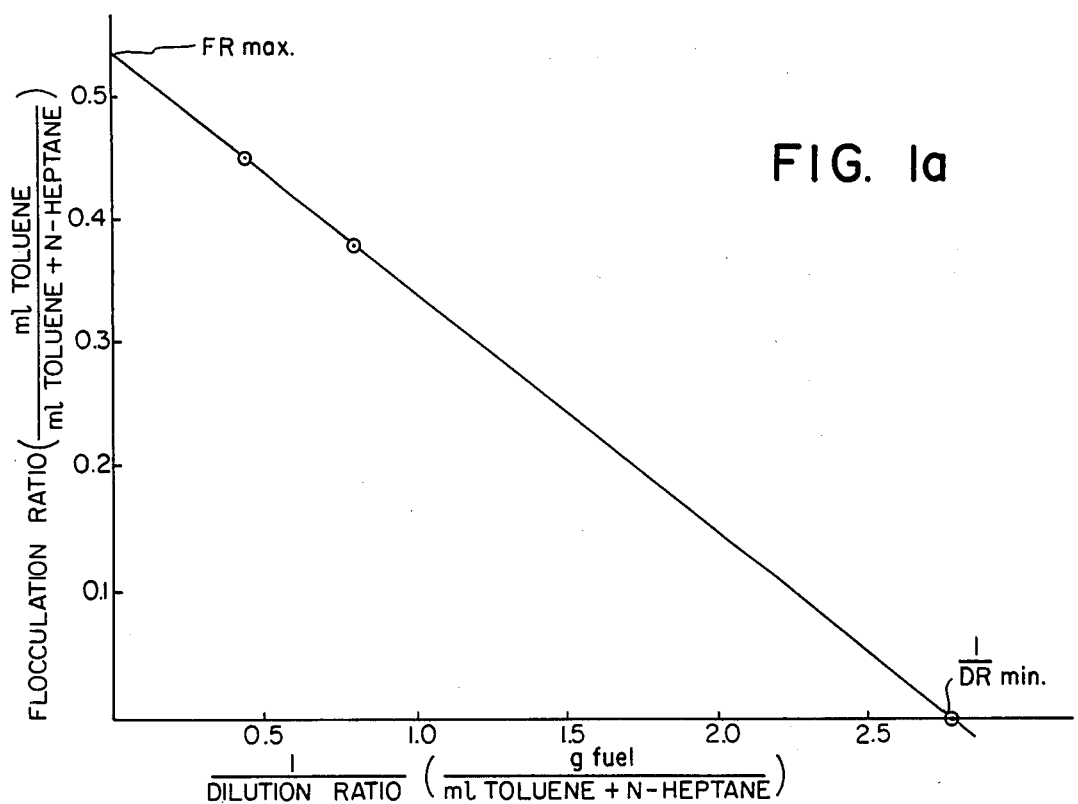
Figure 1B:
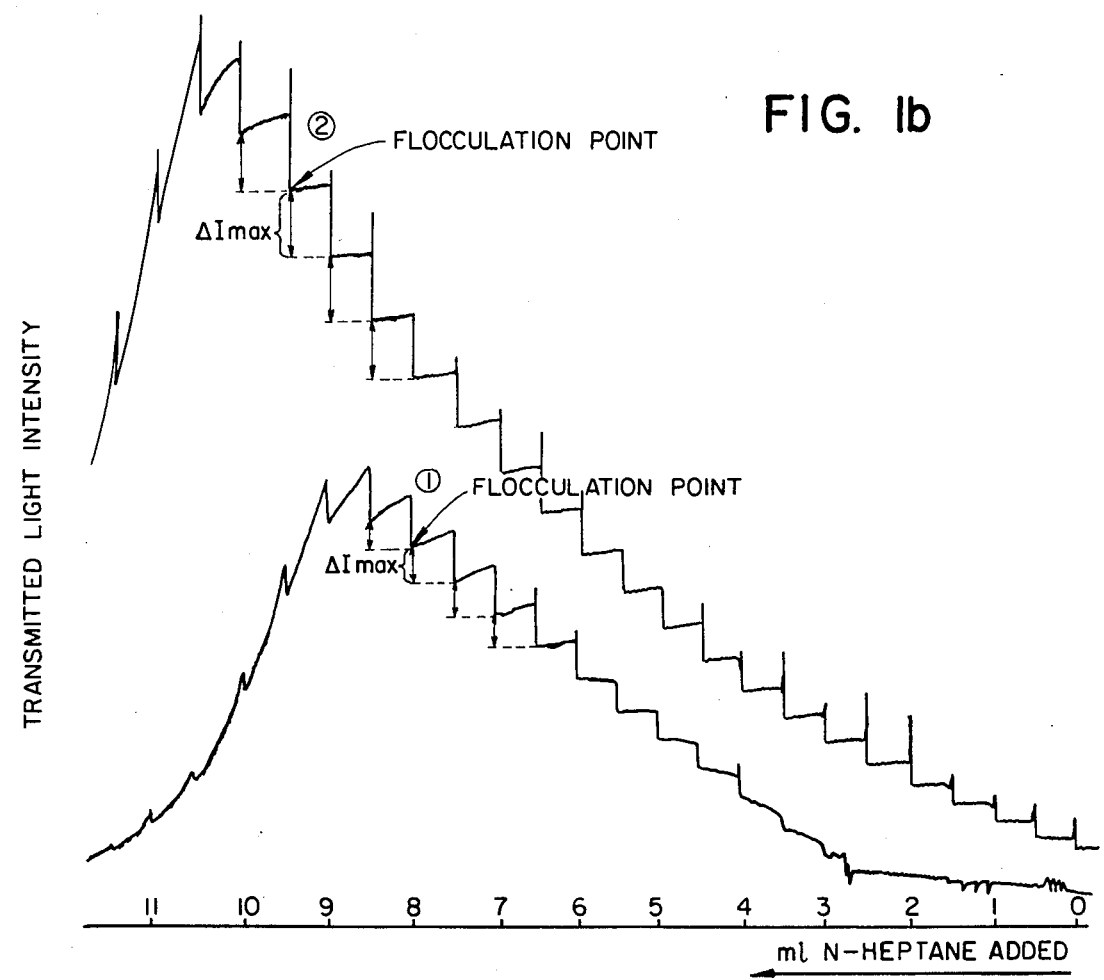

The reproductions of recorder graphs shown in FIG. 1b illustrate how points were obtained to plot FR versus 1/DR as in FIG. 1a for one visbreaker tar fuel. To start with, small volumes of heptane were added stepwise to 22 grams of the fuel, and observations were made with the optical probe of the transmitted light intensity through the diluted fuel as increasing amounts of n-heptane were mixed with the fuel. As more diluent was added, the transmitted light intensity increased stepwise up to a point where a turn-down in transmitted light intensity indicated that flocculation had occurred. The point just short of flocculation is reached when the increment in transmitted light intensity reaches a maximum. In the bottom curve of FIG. 1B the flocculation point was reached when 8 milliliters of n-heptane had been mixed with the 22 grams of fuel. Thus at DR=8 milliliters/22 grams or DR=0.36 milliliters/gram, we have FR=0 milliliters aromatics/8 milliliters aromatics+paraffinics or FR=0. This pair of values was then plotted in FIG. 1a as FR=0 and 1/DR=22/8=2.75.

Next the top curve of FIG. 1b was plotted, using a starting mixture of 5.5 milliliters of toluene and 11.4 grams of fuel. Observations with the optical probe were again made as increasing amounts of n-heptane were mixed with the toluene-fuel mixture. Flocculation was observed to occur just after 9 milliliters of n-heptane were added. Thus at DR=14.5 milliliters/11.4 grams or DR=1.27 milliliters/gram, we have FR=5.5 milliliters aromatics/14.5 milliliters aromatics+paraffinics or FR=0.38. This pair of values was then plotted in FIG. 1a as FR=0.38 and 1/DR=11.4/14.5=0.79.

Similarly a third pair of values for FR and DR were obtained and plotted in FIG. 1a, using a different starting mixture of toluene and fuel.

For a fuel other than the visbreaker tar fuel represented by FIGS. 1a and 1b, one makes observations with the optical probe as in FIG. 1b, obtaining several different curves, each of which curves provides one pair of values for FR and DR to be plotted in a FR vs 1/DR plot as in FIG. 1a.

P values and Flocculation Ratio curves are valuable indicators of the "stability reserve" (excess stability) of a fuel oil. This type of information is particularly useful, e.g. for optimizing conversion in visbreaking and the stability of the tar.

The Reference paper gives a $P_o$ value of 0 for n-heptane and even gives negative values for higher aliphatic hydrocarbons ($C_6$–$C_{16}$). Aromatics have a much higher $P_o$ value (up to 1.5), while naphthenes have a $P_o$ value between aliphatics and aromatics. $P_o$ values for mineral oils are claimed to vary between 0.12 (poor in aromatics) to 1.3 (some aromatic extracts).

If the $P_o$, $P_a$, and P values of a residual fuel and the $P_o$ of a cutter stock are known, then the state of peptization, P, of intermediate fuel oil blends can be calculated by the equations given above.

In order to make observations of the occurrence of flocculation on the basis of light absorption or scattering by the precipitated asphaltenes, a suitable radiation source for measurement of transmitted light intensity in heavy fuel oils must be chosen. On the basis of absorption spectra of diluted fuel samples it was decided to use a light source in the near-infrared. The absorption spectra showed minimal absorption at 730 nm, high absorption in the ultraviolet, and moderate absorption in the near-infrared region. The choice was made for the near-infrared rather than any other spectral region in order to avoid interference from ambient light. A GaAs:Si-light-emitting-diode (IR-LED), which is an inexpensive source of near-infrared radiation with a dominant emission at 950 nm, has been found to be effective for this purpose. The light-emitting diode should have a high luminal flux and small radiation angle. A silicon phototransistor such as Philips BPX25 is used as the detector element for the infrared radiation which has been transmitted through the fuel oil samples. As an alternative, silicon photodiodes with an IR filter such as Siemens BP104 may be used with appropriate optics. The optical system is designed so as to produce a narrow radiation beam when the probe is immersed in fuel with high refractive index.

Optical probe 15, FIG. 2a, is the embodiment of the probe which is used for laboratory observations of the occurrence of flocculation in fuel oils. A different embodiment shown as 25 in FIG. 2b is used when the optical probe is to be employed in a continuously monitoring process analyzer. The electrical circuit for the operation of either embodiment of the optical probe is not illustrated here since it is straightforward standard circuitry for the operation of an IR-LED and a phototransistor of these types and forms no part of this invention. Light is emitted from the IR-LED when the voltage applied to it exceeds the forward voltage of the diode (typically 1.4 volts). The current is appropriately limited by use of an input resistor. Light is detected by the phototransistor, and the voltage developed across a resistor in its output circuit is proportional to the intensity of the detected light.

Embodiment 15, FIG. 2a, comprises stainless steel housing 13 which serves as a support for IR-LED 10 and phototransistor 11 and also as a conduit for leads to those elements. IR-LED 10 resides at the lower end of housing 13 and transmits infra-red radiation upwardly through its window 19a across sample slit 12 to phototransistor 11 through its window 19b. These elements are all set and held in fixed positional relationship with respect to each other by potting resin 17, which may be epoxy or acrylate. Epoxy is in many cases adequate, but for use in highly aromatic solvents at high temperatures it is necessary to resort to an all glass or glass-metal system. An alternate arrangement of these elements has phototransistor 11 at the lower end of housing 13 with IR-LED 10 located above phototransistor 11 and across sample slit 12 therefrom, i.e. interchanged in position from the arrangement shown in FIG. 2a. There is however an advantage in having the elements arranged as illustrated in FIG. 2a since that arrangement achieves better distribution and dissipation of heat within the probe assembly. Heat is generated mainly in IR-LED 10 and its input resistor, wire wound resistor 14, and the arrangement as in FIG. 2a provides greater spacing between these heat generating circuit elements. The radiation efficiency of IR-LED 10 and the sensitivity of phototransistor 11 are temperature dependent. To avoid fluctuations in radiation power and detector sensitivity during the measurements it is important to maintain a constant temperature. Since the probe is to be partly immersed, as described further below, in a bath of thermostated oil, this requirement is fulfilled by improving the distribution and dissipation of heat within the probe assembly as in the arrangement of FIG. 2a.

Sample slit 12 in this embodiment has an optical path length of about 2 mm. In an embodiment based on scattered radiation rather than transmitted radiation it is to be understood that the radiation detector (e.g. phototransistor) is located to the side rather than in a straight line with the source and sample.

FIG. 2c illustrates in more detail the construction and operation of the IR-LED-slit-phototransistor assembly, showing how the optoelectronic components of the probe are securely protected against aromatic fuel invasion. IR radiation is emitted from IR-LED 10, passes through IR-LED glass lens 9a, an air space 6a, IR-LED glass window 19a, sample slit 12, phototransistor glass window 19b, another air space 6b, and phototransistor glass lens 9b and reaches phototransistor 11. IR-LED 10 is housed in IR-LED tubular housing 7a, and phototransistor 11 is housed in phototransistor tubular housing 7b. Inner seals of potting resin 17a, sealing components 10 and 11 to the glass windows, protect the IR-LED and phototransistor and are not in direct contact with the oil. If a failure resulting from exposure to aromatic fuel oil should occur in the potting resin it would be in the outer seals 17b which fill the edges of glass windows 19a and 19b and stainless steel housing 13, and these outer seals can easily be replaced. Such a seal failure, if it should occur, would not result in probe failure, since the probe optoelectronic components are protected by inner seals 17a which serve as second lines of defense.

FIG. 2c further illustrates the optical features of the probe, whereby the IR light is concentrated into cones of small angle at both the IR-LED and the phototransistor. It will be understood that narrowing of the IR light beam is desired in order to concentrate the available IR radiation into a small cross-sectional area and thus, by maximizing the IR radiation per unit area, achieve a maximum signal to noise ratio. This is particularly desirable when detecting radiation transmitted through a strongly absorbing medium such as a heavy fuel oil. Further, by having all the IR light concentrated into a small area it is possible to reduce the viewing angle of the phototransistor to an angle no greater then is needed to view that area; this is advantageous since the smaller the viewing angle of the phototransistor, the less undesirable secondary effects of scattered and reflected radiation will be encountered. Still another advantage of limiting the angles of the cones of emitted and collected IR light is that minimizing the angle of incidence of IR light on the glass windows also minimizes the amount of light reflected from the glass surfaces thereof, and this minimizes the amount of light which finds its way to the phototransistor by "ghost" paths, e.g. by refraction through the slit seal. It is important to minimize the light that arrives by such "ghost" paths since such light adds to the phototransistor dark current and thereby limits the operating absorbance range of the probe. As additional protection against light transmitted by such "ghost" paths the slit seal is made strongly absorbing (e.g. by adding carbon-black to the epoxy sealing material).

Air space 6a between lens 9a and window 19a acts as an "air lens" and serves to maintain lens 9a effective for narrowing the light beam. If there were no "air lens" at this point, and the light emanating from lens 9a directly entered the sample oil, which typically has a high refractive index, the beam narrowing property of lens 9a would be nullified. The same reasoning applies with respect to "air lens" 6b at the phototransistor.

Printed circuit boards 8 are also shown in FIG. 2c.

The use of probe 15 in making laboratory measurements of fuel oil stability is illustrated in FIG. 3. The lower end of probe 15 is immersed in fuel oil sample 30 so that the fuel oil resides in or flows through slit 12. The occurrence of flocculation in the fuel oil within slit 12 is observed as a lessening of transmitted light intensity from IR-LED 10 to phototransistor 11. Electrical connections are made to the IR-LED and the phototransistor as shown in FIG. 2a where 16a represents the electrical leads to the IR-LED and 16b the leads to the phototransistor.

The stability of fuel oils, as indicated by the conditions necessary to initiate flocculation, is determined as illustrated in FIG. 3 by immersing probe embodiment 15 in the sample 30 of fuel oil or fuel oil-diluent mixtures contained within container 31 which is surrounded by water bath 32. Water bath 32 is maintained at a desired temperature by heating it on hot plate 34 and monitoring the temperature with thermometer 35. Sample 30 is continuously stirred such as by magnetic stirrer 33 in order to present a representative sample at slit 12 of the optical probe. An appropriate titrating fluid such as n-heptane is added with a titration buret 36. Power supply 37 supplies the electrical power to operate the IR-LED. Millivolt meter or recorder 38 measures the output from the phototransistor 11 in optical probe 15.

Continuous Measurement

Figure 4:
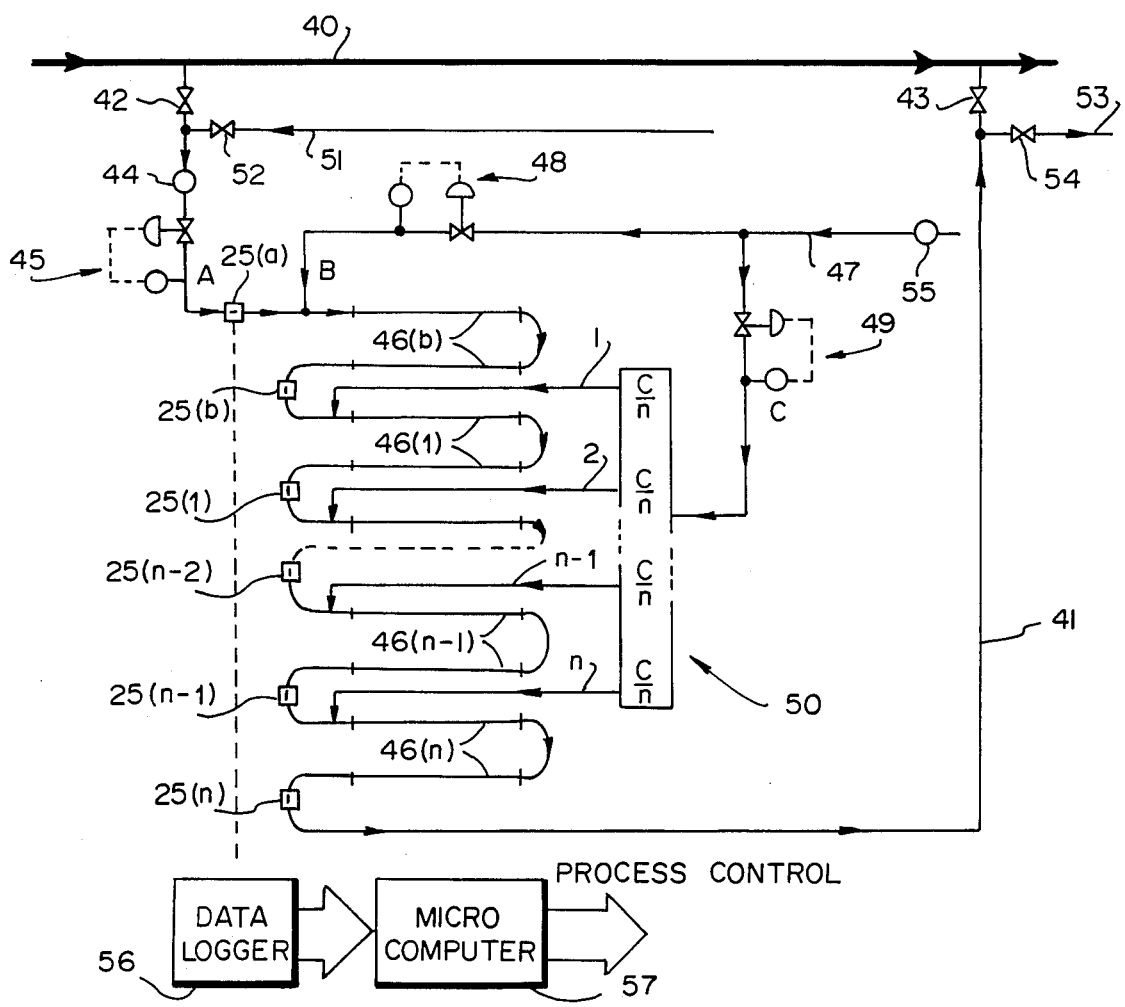
FIG. 4 is a schematic representation of the apparatus of the invention for making continuous measurements as in on-line process control.

The optical probe and the titration procedure described above for determining stability characteristics of fuel oils lend themselves also to the design of a continuously monitoring process analyzer. FIG. 2b illustrates optical probe embodiment or optical cell 25 for use in a process analyzer, comprising the same essential elements as the optical probe 15 of FIG. 2a, namely, an IR-LED 20 and a phototransistor 21, which serve in embodiment 25 in the same way as IR-LED 10 and phototransistor 11 in embodiment 15. Optical cell 25 comprises also a short section of glass pipe having flanged ends or other means for assembly in the sample piping or conduit of the process analyzer and having a narrowed down or slit portion 22 with IR-LED 20 on one side and phototransistor 21 on the other side of the slit portion 22 of the optical cell. Infrared radiation from IR-LED 20 must traverse the fuel oil sample within slit 22 to reach phototransistor 21. Once again, as in embodiment 15, the occurrence of flocculation in the flowing stream of fuel oil in embodiment 25 is observed as a reduction in the transmitted light intensity from IR-LED 20 to phototransistor 21. IR-LED 20 is supported within support 23, and its electrical leads are indicated at 26a. Phototransistor 21 is supported within phototransistor housing 28 and its electrical leads are indicated at 26b. FIG. 4 illustrates schematically how such a process analyzer operates to monitor the stability of fuel oil flowing through line 40. A sample of the line fuel is continuously drawn off as constant flow sample stream A through sample loop or conduit 41. The sample is drawn into the loop through inlet valve 42 and out of the loop back into line 40 through outlet valve 43. The loop sample is driven at a constant flow rate by pump 44 under the control of flow control 45. The sample then flows in order through optical cell 25a (which is one such probe or cell as illustrated in FIG. 2b), static mixers 46b, optical probe 25b, static mixers 46(1), optical probe 25(1), and so forth through successive pairs of optical probes and static mixers until the sample emerges from static mixers 46(n) and optical probe 25(n). Non-aromatic diluent flows in line 47 under the action of pump 55. This stream of non-aromatic diluent splits into two streams, one under the control of diluent increment flow control 49 and the other stream under the control of predilution flow control 48. The stream controlled by flow control 49 flows at a constant rate C and enters constant flow distributor 50, which is a branching device to provide, as illustrated in FIG. 4, n different equal streams 1, 2, . . . n−1, and n, each of which is introduced into loop 41 at a different point as next explained. Stream 1 enters loop 41 in which the sample is flowing just after the sample has emerged from optical probe 25(b) and before it enters static mixers 46(1). Stream 2 similarly enters the loop after the sample emerges from optical probe 25(1) and before it enters the next static mixers. These increments of non-aromatic diluent, all having equal rates of flow, are thus added to the sample stream in bypass loop 41, thoroughly mixed with the sample in the loop, and the mixture is passed sequentially through optical probes 25(1), . . . 25(n).

Just as with the embodiment for laboratory use illustrated in FIGS. 2a and 3, the occurrence of flocculation of asphaltenes in the stream in process analyzer loop 41 is observed optically by the occurrence of a decrease of transmitted light intensity as observed at the several optical cells 25. Data on the observations of transmitted light intensity are collected and passed to data logger 56 programmed for determination of flocculation points based on the maximum increment in transmitted light intensity as in the description above for Laboratory or Batch Measurement. The output of data logger 56 may be transmitted into a microcomputer 57 programmed such that process control (e.g. control of the temperature of a thermal cracker unit) can be implemented therefrom.

If it is desired to precondition the sample flowing in loop 41 to bring its flocculation point within the range of the n stages of increments, a portion of non-aromatic diluent stream in line 47 may be added as constant flow B through the branch which is under the control of flow control 48. Constant flow B enters the loop stream just after the sample emerges from optical probe 25(a) and before it enters static mixers 46(b).

There is also provided a rinsing fluid line 51 with rinsing fluid inlet valve 52 for the purpose of rinsing the entire bypass loop system 41 with aromatic diluent when so desired. Also rinse line 51 may be used for predilution of the flowing sample in loop 41 with aromatic diluent.

The sample flowing in loop 41 after it has been analyzed can be routed back into fuel line 40 through outlet valve 43 or can be routed into a slop line 53 through slop outlet valve 54.

Figure 5:
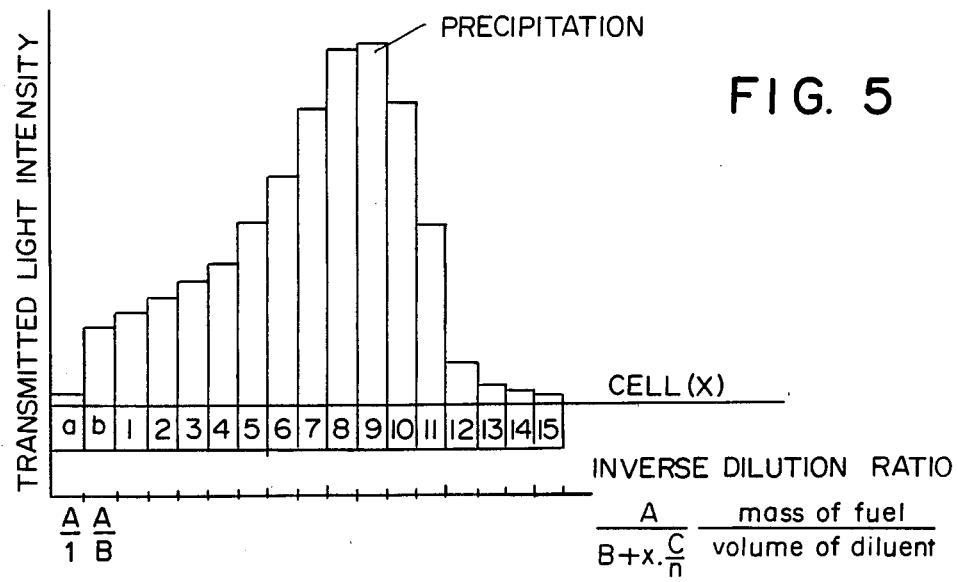
FIG. 5 illustrates the data assembled by the apparatus of FIG. 4, by which the stability properties of colloidal systems are detemined and can be used for process control.

Once again, a process analyzer is described and is illustrated schematically in FIG. 4 for determining the stability reserve of fuel, resid upgrading stocks, or products, employing an automated adaptation of the laboratory type optical probe and titration procedure described earlier herein. The process analyzer may be installed on a by-pass loop of a process or feed line. A constant flow A of the stream to be analyzed is routed along a number (a, b, 1 to n) of optical probes or cells, each containing the same basic elements as that used in the laboratory procedure earlier described. After predilution with a constant flow B of non-aromatic diluent the mixture is passed through static mixers to homogenize the fluid and allow for the required response time. Light transmitted through the undiluted fuel is checked by optical cell 25($a$), and the prediluted fuel by cell 25($b$). After cell 25($b$) the fuel is further diluted, in sequential steps, with a constant flow C/n of non-aromatic diluent per step. After each dilution step and after passage through that step's associated static mixer, the fuel undergoes a transmitted light intensity check by the optical cell associated with the step. The increase in size of asphaltene particles (when flocculation occurs) causes an increase in light absorption. The flocculation point, upon dilution with non-aromatic diluent, is thus marked by a decrease in transmitted light intensity, relative to the light intensity which would normally be observed from the sequential dilutions of the fuel. Typical transmitted light intensity levels detected by the optical cells are shown in FIG. 5, for a fuel which shows precipitation of asphaltenes at an inverse dilution ratio equal to A divided by the quantity B+9(C/n). The flocculation point thus determined is between A divided by the quantity B+8(C/n) (the inverse dilution ratio at which precipitation just fails to occur) and A divided by the quantity B+9(C/n).

Viscosity Blending

Figure 1C:
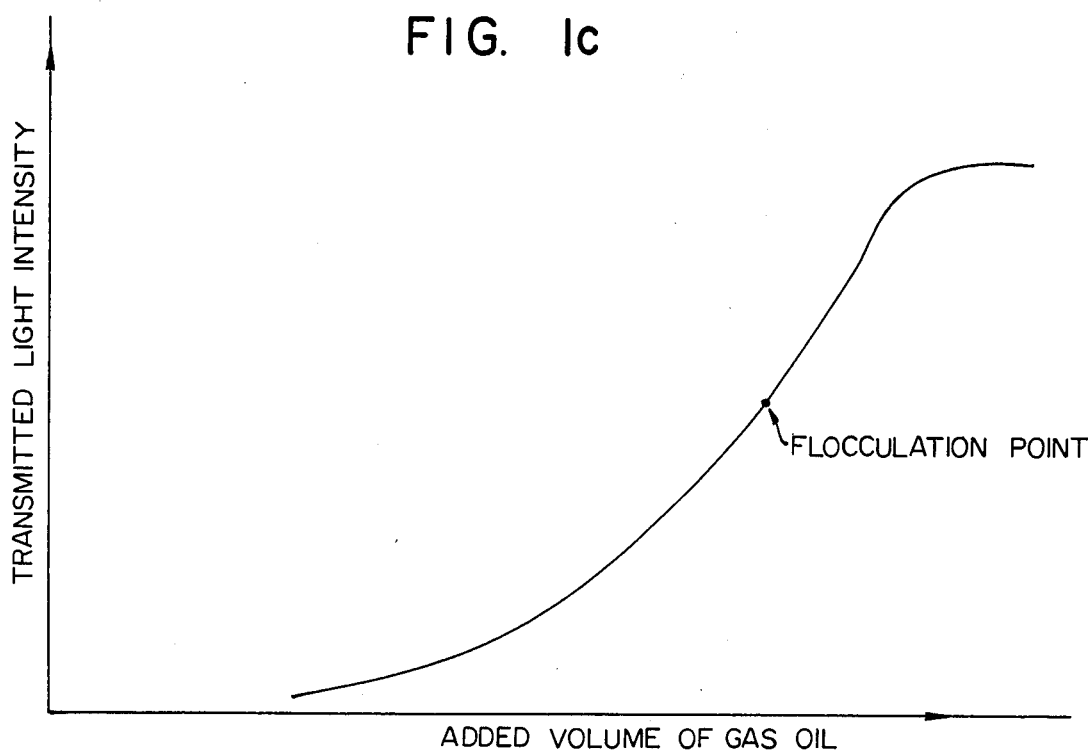

The optical probe is useful in determining how much diluent can be blended into a heavy fuel without exceeding the stability limit. FIG. 1c shows the titration curve for transmitted light intensity as measured by the probe versus the volume of gas oil added to a heavy fuel oil. The onset of flocculation is marked by reaching the maximum slope in the titration curve (largest output increase between two successive additions; this is the same criterion as used hereinabove in connection with FIGS. 1a and 1b).

Storage Stability and Compatibility

The storage stability of residual fuels and their compatibility with other fuel oils and with gasoils is mainly determined by the state of peptization P of the asphaltenes present in such systems. The state of peptization in turn depends on the peptizability $P_a$ of the asphaltenes and the peptizing power $P_o$ of the oil matrix. These parameters may be derived from the linear relationship between the flocculation ratio (FR) and the inverse of the dilution ratio (DR).

Figure 1D:
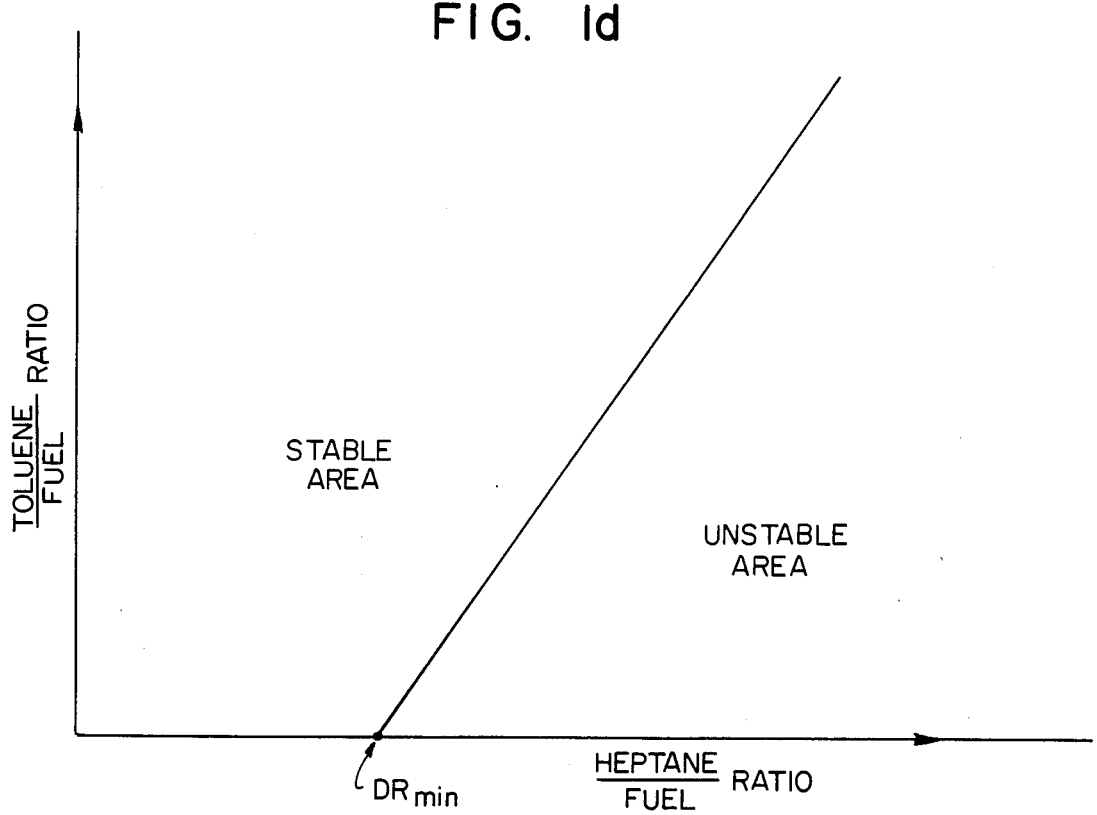

An alternative and easier way to derive these parameters is by use of the linear relationship shown in the toluene-heptane graph of FIG. 1d. The intercept on the n-heptane axis gives the stability reserve ($DR_{min}$) of the fuel oil. The slope of the stability line depends only on the asphaltenes peptizability $P_a$:

$$\text{slope} = (1 - P_a)/P_a$$

In practice a slope close to one is usually found ($P_a$ = approx. 0.5).

For a fuel oil with no stability reserve ($DR_{min}=0$; P=1) a straight line through the origin is obtained in the toluene-heptane plot.

While I have chosen to illustrate and describe certain preferred embodiments of my invention, this is not to be considered as limiting but as illustrative only.

Therefore, what is claimed as new, and is desired to be secured by Letters Patent is:

1. Apparatus for continuously determining the ratio of diluent to colloidal fluid at which flocculation occurs in a mixture of said diluent and said fluid comprising in combination
    a conduit for said fluid,
    means for causing said fluid to flow through said conduit at a predetermined rate,
    means for adding said diluent at a measured incremental rate to said fluid at each of a plurality of successive positions along said conduit to make successive trial mixtures of said diluent and fluid,
    monitor means located downstream of each said diluent-adding position along said conduit for generating an electrical signal indicative of the ability of each said trial mixture of diluent and fluid to transmit radiation, and
    means for collecting said electrical signals and automatically computing therefrom the ratio of diluent to colloidal fluid at which flocculation occurs in a mixture of said diluent and said fluid.

2. Apparatus for continuously determining the ratio of diluent to colloidal fluid at which flocculation occurs in a mixture of said diluent and said fluid comprising in combination
    a conduit for said fluid,
    means for causing said fluid to flow through said conduit at a predetermined rate,
    means for adding said diluent at a measured incremental rate to said fluid at each of a plurality of successive positions along said conduit to make successive trial mixtures of said diluent and fluid,
    monitor means located downstream of each said diluent-adding position along said conduit for generating an electrical signal indicative of the characteristic of each said trial mixture of diluent and fluid to transmit radiation, and
    means for collecting said electrical signals and automatically generating therefrom control signals for the control of the process from which said colloidal fluid is derived in order to adjust the flocculation properties thereof to predetermined values.

3. Apparatus for determining the point at which flocculation occurs during the progressive intermixing of amounts of a diluent flocculating liquid with a colloidal fluid, which apparatus includes:
    an elongated conduit having inlet and outlet ends,
    colloidal fluid flowing means communicated with said conduit inlet end to deliver a substantially constant volume stream of colloidal fluid into said conduit,
    a plurality of injector ports opening into said elongated conduit intermediate the respective inlet and outlet ends thereof,
    diluent flocculating liquid metering means communicated with the respective injector ports, being operable to introduce incremental amounts of diluent flocculating liquid through the respective injector ports and into said constant volume colloidal liquid stream, and monitor means including a monitor station positioned intermediate each pair of adjacently positioned injector ports, so that the character of the colloidal, constant volume liquid stream between adjacently positioned injector ports can be tested to determine if flocculation has occurred in said stream at any monitor station.

4. In the apparatus as defined in claim 3, wherein said monitor means includes; means for concurrently irradiating the colloidal liquid stream in said conduit at each monitor station, and for concurrently measuring the amount of irradiation which transverses the irradiated stream at each said monitor station.

5. Apparatus as defined in claim 4, wherein said means for concurrently irradiating the colloidal liquid stream is a source of near infrared radiation.

6. In the apparatus as defined in claim 3, wherein the respective injector ports are equispaced longitudinally apart along said conduit.

7. In the apparatus as defined in claim 3, wherein each said monitor station is positioned in the conduit immediately upstream of one of said injector ports.

8. In the apparatus as defined in claim 3, wherein said monitor means includes; a signal generating means associated with each monitor station to generate a signal in response to the degree of flocculation which occurs at said monitor station.

9. In the apparatus as defined in claim 3, wherein each monitor station in said conduit includes; a wall section thereof which is translucent to the colloidal liquid stream, and which is translucent to radiation.

10. In the apparatus as defined in claim 9, wherein each monitor station in said conduit constitutes a constricted section.

11. In the apparatus as defined in claim 9, wherein each monitor station in the conduit includes a constricted segment formed of a material which is translucent to a beam of radiation, and each monitor station includes a source of radiation disposed at one exterior side of the conduit constricted segment, and a radiation collector disposed at the opposed side thereof.

12. In the apparatus as defined in claim 3, wherein said conduit includes a plurality of substantially equispaced injector ports and a monitor station disposed intermediate each adjacent pair of injector ports.

13. In an apparatus as defined in claim 3, wherein said conduit includes a plurality of substantially equispaced injector ports, and a monitor station disposed adjacent to and downstream of each injector port.

14. In an apparatus as defined in claim 3, including means communicated with said conduit inlet for injecting a constant flow of said diluent flocculating liquid into said colloidal liquid stream, prior to the introduction of incremental amounts of flocculating liquid thereto.

* * * * *